US00PP33309P2

(12) United States Plant Patent
Hansen

(10) Patent No.: US PP33,309 P2
(45) Date of Patent: Aug. 3, 2021

(54) ***HIBISCUS* PLANT NAMED 'SPINDERELLA'**

(50) Latin Name: ***Hibiscus* hybrid (L.)**
Varietal Denomination: Spinderella

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,046

(22) Filed: Feb. 23, 2021

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

*Primary Examiner* — Keith O. Robinson

(57) ABSTRACT

A new and distinct cultivar of winter-hardy, herbaceous, perennial, hybrid *Hibiscus* plant named 'Spinderella' comprising a compact, dense, mounded habit of multiple, well-branched, basal stems producing flowers from the bottom to the top of the plant from late July to frost. Flowers have petals that are broadly-overlapping, with deeply impressed veins of white radiating through the center that intensifies to a medium pink on the leading edge. The foliage is simple and ovate, with a crenulate margin and deep-green with greyed-purple blotches.

2 Drawing Sheets

Botanical classification: *Hibiscus* hybrid (L.).
Variety denomination: 'Spinderella'.

STATEMENT REGARDING PRIOR DISCLOSURES UNDER 37 CFR 1.77(b)(6)

The first non-enabling disclosures were a brief description and photograph of the new plant on Dec. 1, 2019 on the website operated by Walters Gardens, Inc. followed by a listing in the "Walters Gardens 2020-2021 Catalog" that was first distributed on May 20, 2020. The first disclosure, in the form of a sale, was made by Walters Gardens, Inc. on Apr. 13, 2020. Walters Gardens, Inc. obtained the new plant and all information relating thereto, from the inventor. No plants of *Hibiscus* 'Spinderella' have been sold, in this country or anywhere in the world, by any name, nor has any disclosure of the new plant been made more than one year prior the filing date of this application, and such sale or disclosure within one year was either derived directly or indirectly from the inventor.

BACKGROUND AND ORIGIN OF THE PLANT

The present invention relates to the new and distinct hardy, herbaceous, *Hibiscus* plant, *Hibiscus* 'Spinderella' hybridized under direction of the inventor Aug. 10, 2015 at a wholesale perennial nursery in Zeeland, Mich. The new plant is a cross between the unreleased, proprietary hybrid known as 12-07-1 (not patented) times 'Vintage Wine' U.S. Plant Pat. No. 27,839. Into the trial process the new plant was assigned the breeder code labeled 15-66-2. The parent has a complex mixture of species in them, comprising the species: *moscheutos* and *coccineus*.

*Hibiscus* 'Spinderella' was first asexually propagated in late summer of 2017 by sterile shoot-tip tissue culture and later by shoot tip cuttings at the same nursery in Zeeland, Mich. The resultant asexually propagated plants have been found to be stable and true to type in successive generations of asexual reproduction.

BRIEF SUMMARY OF THE PLANT

*Hibiscus* 'Spinderella' differs from its parents as well as all other hardy herbaceous *Hibiscus* known to the applicant in many traits. The most similar *Hibiscus* cultivars known to the applicant are: 'Tie Dye' U.S. Plant Pat. No. 24,078, 'Starry Starry Night' U.S. Plant Pat. No. 27,901, 'Cherry Choco Latte' U.S. Plant Pat. No. 30,738 and 'Turn of the Century' (not patented).

'Tie Dye' has a taller, broader more open habit, the flower is flatter and the leaves are heterophyllous with many being tri-lobed and penta-lobed. 'Starry Starry Night' has a larger habit with darker greyed-purple, smaller, tri-lobed, the flower petals are less imbricate with a larger white portion and reddish pink veining. 'Cherry Choco Latte' has slightly shorter habit, more purplish-mahogany tinted foliage, and flowers with deep magenta veins on a near white background, petals with leading edges folded under. 'Turn of the Century' has a taller and more open habit; tri-lobed to penta-lobed lighter green foliage; and smaller, less rounded flowers; petals are less imbricate with thinner substance, and a center eye that is more orangish-red and less dark red, petal veins are closer together and pinkish colored, and the pollen is yellowish-grey.

The female parent plant is less compact in habit and the foliage was much darker greyed-purple. 'Vintage Wine' has a taller and more open habit with dark scarlet-red flowers and the foliage is broader.

*Hibiscus* 'Spinderella' is a unique hardy herbaceous *Hibiscus* with the following combined traits:

1. Winter-hardy perennial with compact, dense, mounded habit of multiple, well-branched, basal stems;

2. Many rotate flowers with a dark red eye, medium pink intensified distally and toward the leading petal edge and white near the eye and veins radiating toward the edges;
3. Petals are overlapping and impressed at veins giving extra strength and resistance to wind damage;
4. Flowers produced over a long period from late July to frost;
5. Foliage is ovate and simple with a crenulate margin and deep-green with greyed-purple color in blotches.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plants in the photographs are from a four-year-old plant in an outdoor trial garden in Zeeland, Mich.

DETAILED BOTANICAL DESCRIPTION

Figure 1:
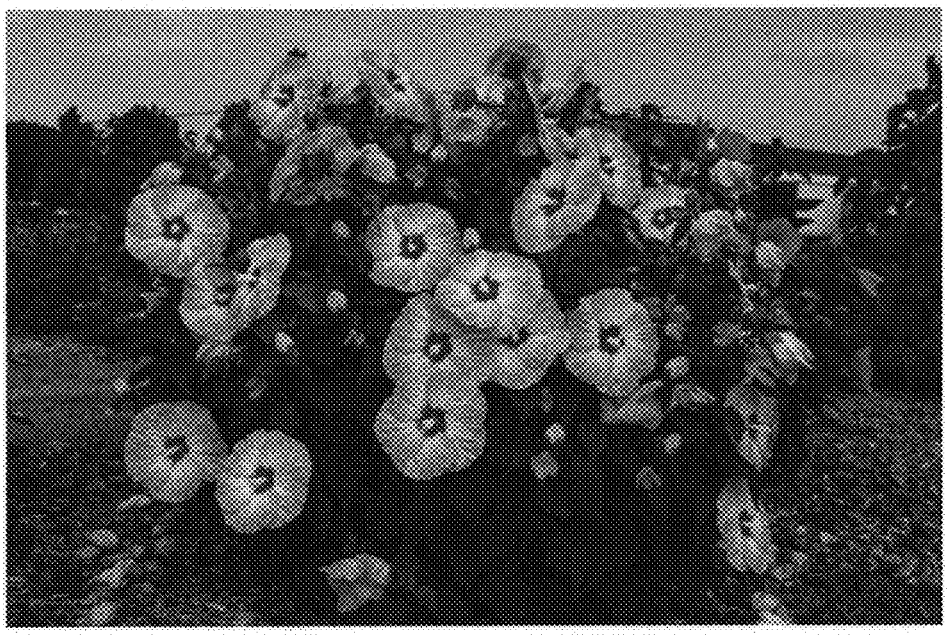
FIG. 1 shows the landscape habit of the new plant in full flower.
Figure 2:
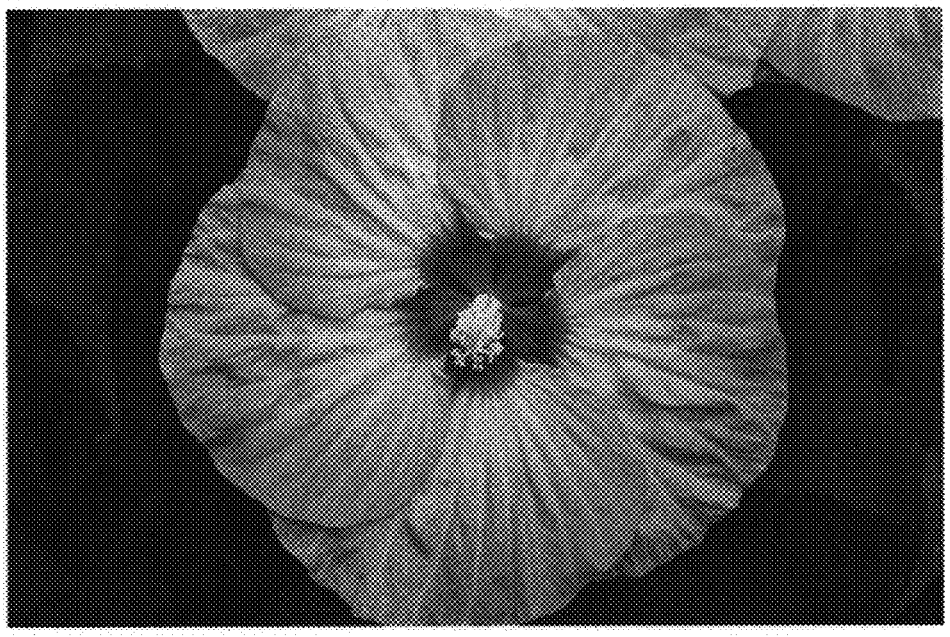
FIG. 2 shows a close-up of the flower.
Figure 3:
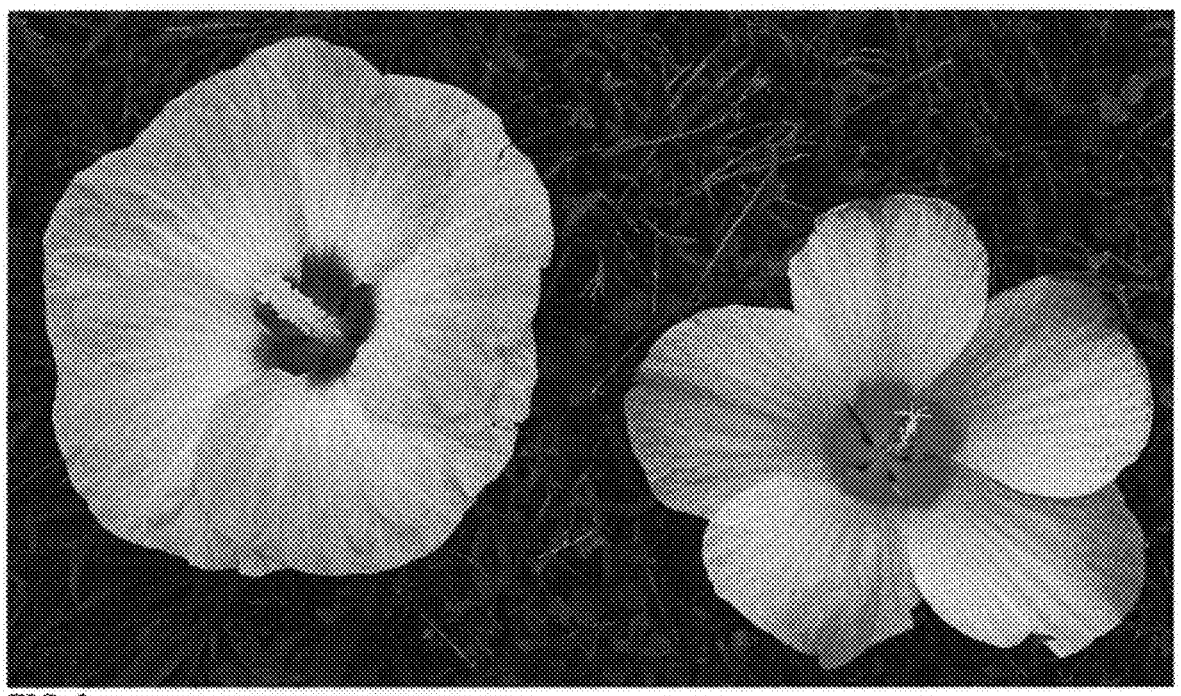
FIG. 3 shows a comparison of the flower of 'Spinderella' on the left and 'Turn of the Century' on the right.

The following descriptions and color references are based on the 2015 edition of The Royal Horticultural Society Colour Chart except where common dictionary terms are used. The new plant, *Hibiscus* 'Spinderella', has not been observed under all possible environments. The phenotype may vary slightly with different environmental conditions, such as temperature, light, fertility, moisture and maturity levels, but without any change in the genotype. The following observations and size descriptions are of four-year-old plants in the loamy-sand, open-field full-sun trials of a nursery in Zeeland, Mich. with supplemental fertilizer and water as needed. The plants are of natural habit and were not treated with plant growth regulators, nor were they pinched at any time in the growth year.

Parentage: The female or seed parent is the unreleased, non-patented, proprietary *Hibiscus* known by the breeder code 12-07-1, the male or pollen parent is 'Vintage Wine';

Propagation:

*Method*.—Shoot tip cuttings and sterile shoot-tip plant tissue culture division.

*Time to initiate roots from tissue culture*.—About two weeks.

*Rooting habit*.—Normal, branching, developing thick to about 1.8 cm diameter, fleshy; root color creamy yellow nearest RHS 158C depending on soil type.

*Crop time*.—Under normal summer growing conditions 12 to 16 weeks to flower in a four-liter container from cutting. Plant vigor is very good.

Plant description:

*Plant habit*.—Hardy herbaceous perennial with about five thick, upright, heavily-branched stems producing an upright spreading mound to about 93.0 cm tall and about 102.0 cm wide; flowering from base to top of plant with up to about 16 flowers in the upper main stem and up to 50 total flowers on all the branches of a single stem.

*Stem*.—Terete, glabrous, glaucous; to about 90.0 cm tall and about 2.2 cm diameter at base, average about 82.0 cm tall and about 2.8 cm diameter at base.

*Stem color*.—Proximal main stems nearest RHS 138A; distal main stems blend between RHS 147B and RHS 183B.

*Lateral branches*.—5 to 11 per stem, average about 8 per stem; terete; glabrous; glaucous; to about 38.0 cm long and 0.9 cm diameter at base, smaller distally.

*Lateral branch color*.—Proximally nearest a blend between RHS 138B and RHS 183D; distally nearest a blend between RHS 147B and RHS 187B.

*Internode*.—About 6 nodes per stem below branches and 8 below single flowers; average about 30 nodes per stem; internode length about 3.1 cm of unpinched plant.

*Internode color*.—Same as surrounding stem.

Foliage description: Ovate; alternate; crenulate; apex narrowly acute to nearly apiculate; base cordate; micro-puberulent adaxial and adaxial glabrous; not incised; adaxial and abaxial surfaces dull; leaf blades to about 21.5 cm long and about 12.4 cm across, average blade size 16.0 cm long and 10.0 cm wide; no fragrance detected;

*Foliage color*.—Young expanding leaves — adaxial variable blotches between RHS 137A and RHS N187A, abaxial nearest RHS 147C; mature leaves — adaxial nearest RHS NN137B, blotched randomly with nearest RHS N187A, abaxial nearest RHS 147B.

*Veins*.—Palmate; dull adaxial and abaxial; slightly applanate adaxial, costate on abaxial; micro-puberulent adaxial and abaxial.

*Vein color*.—Young adaxial nearest RHS 187B and abaxial nearest RHS 183D; mature adaxial midrib between RHS 187B and RHS 187C, secondary veins nearest RHS 185B, abaxial between RHS 176B and RHS 182C.

*Petioles*.—Cylindrical distally and proximally slightly applanate adaxial to abaxial, glabrous; to about 8.2 cm long and 6.0 mm diameter at base, average about 6.0 cm long and 5.0 mm wide at base.

*Petiole color*.—Young and mature adaxial between RHS 166A and RHS N186C; abaxial between RHS 176C and RHS 146C.

Flower description: Complete; actinomophic; mostly outwardly facing; rotate; to about 22.0 cm across and 5.5 cm deep, decreasing distally; with a reddish center eye with short radiating veins about 5.8 cm across;

*Buds one day prior to opening flat*.—Ellipsoidal with rounded apex and bluntly truncate base; sepals proximally adpressed to petals and distally slightly flaring; to about 6.5 cm long and about 4.4 cm diameter in middle; petals tightly closed at apices.

*Bud color one day prior to anthesis*.—Exposed petal color nearest RHS 56B with exposed petal margin nearest RHS 63A and calyx nearest RHS 146B.

*Epicalyx*.—Nine to eleven per flower; linear; margin micro-ciliolate, glabrous; micro-puberulent abaxial and adaxial; sharply acute apex and truncate base, arcuate upwards near apex; about 2.5 cm long and about 4.0 mm wide at base.

*Epicalyx color*.—Adaxial between RHS 146B and RHS 146C with margins nearest RHS 137B, abaxial nearest RHS 137B.

*Calyx*.—Campanulate, form star-shaped hypanthium; to about 2.0 cm deep and 8.0 cm wide at apices.

*Sepals*.—Five, acuminate apex; glabrous; margin entire, edentate; abaxial and adaxial surfaces matte; about 4.2 cm long, about 2.5 cm wide near middle, fused in basal 2.0 cm.

*Sepal color*.—Adaxial base between RHS 146D and RHS 145A, distally nearest RHS 146B with veins of nearest RHS 145C; abaxial nearest RHS 146B with veins between RHS 195B and RHS 195A.

*Inflorescence*.—Solitary, up to 66 per branched stem without pinching; nearly flat face; mostly outwardly facing.

*Flower lastingness*.—Persist for one to two days; effective for at least 6 weeks beginning late July.

*Flower fragrance*.—No detectable fragrance.

*Petals*.—Five; claw-like with broad limb; micro-puberulent adaxial except adaxial eye zone lustrous, remaining distal adaxial portion and entire abaxial glabrous and matte; adnate to the androecium to form a column, leading edge (inside) frequently folded under between 3.0 to 10.0 mm; imbricate to about 110% to 125% overlapping at widest part (petals overlapping 10% to 25% the petal two positions over); margin entire with moderate undulations; palmately veined, primary veins deeply impressed and pleated on adaxial and slightly costate abaxial; surface moderately rippled; apex rounded with distinct basal claw and limb.

*Petal size*.—To about 16.0 cm across and about 10.8 cm long, claw base about 9.0 mm across (smaller in later part of flowering season); reddish eye extending about 2.4 cm from base with veins extending about 4.0 mm beyond eye.

*Petal color*.—Adaxial distal portion and on leading edge nearest RHS 68A and between RHS N155B and RHS NN155A, the dark red eye portion nearest RHS 59B distally toward perimeter, veins nearest RHS 53A near eye and then RHS NN155D distally, and base nearest RHS 46B; middle portion between RHS N155B and RHS NN155A near eye and developing to nearest RHS 68A on leading and distal petal edge; abaxial 3.0 mm wide center nearest RHS NN155D, then distally nearest RHS 155A, progressing to NN155D in the middle portion and distal and leading edge nearest RHS 68B with veins nearest RHS 155A proximally and becoming nearest RHS NN155C distally.

*Gynoecium*.—Single; partially enclosed in column; Staminal column: micro-puberulent and lustrous; about 4.5 cm long and about 1.0 cm across at base; with pistil exserted about 8.0 mm above top of column; Column color: without anthocyanins, nearest RHS NN155B; Style: cylindrical; nearly completely enclosed in column; micro-puberulent in region above staminal column, glabrous within column; about 5.7 cm total length, exserted above column in distal 13.0 mm, penta-furcate in about distal 7.0 mm, branch diameter about 1.0 mm and arcuate upwards distally; color nearest RHS NN155B; Stigma: typically five; flattened globose; puberulent; about 4.0 mm in diameter and 1.5 mm tall; color between RHS 19C and RHS 19D; Ovary: superior; inverted conic; slightly longitudinally grooved; acute apex and truncate base; about 16.0 mm across at base and about 11.0 mm tall; color nearest RHS 145D.

*Androecium*.—Numerous, approximately 100 to 140; Filaments: terete; lustrous and glabrous; arcuate toward stigma; covering almost entire column; to about 5.0 mm long and about 0.35 mm diameter; color nearest RHS NN155B; Anthers: reniform; basifixed; longitudinal; about 2.3 mm long and 1.8 mm across and about 0.8 mm thick; color nearest RHS 18D; Pollen: abundant, globose, less than 0.1 mm long; color nearest RHS 18C.

Pedicel: Terete; micro-puberulent in proximal portion; slightly glaucous; average length from base of sepal to abscission point about 20.0 mm long, from abscission point to stem node about 55.0 mm long; about 5.0 mm wide; longer on early flowers and decreasing in distal flowers; from abscission later to node or base;

Pedicel color: Between RHS 145B and RHS 146C proximally, and becoming between RHS 146D with nearest RHS 178C distally;

Peduncle: Terete; glabrous: glaucous; to about 90.0 cm tall and about 22.0 cm diameter at base, average about 82.0 cm tall and about 1.7 cm diameter at base;

Peduncle color: Proximal main stems nearest RHS 138A; distal main stems blend between RHS 147B and RHS 183B;

Fruit and seed: None observed, but not tested for sterility;

Resistance: *Hibiscus* 'Spinderella' has not displayed any pest and disease susceptibility or resistance beyond that typical of hardy perennial hibiscus.

Culture: The plant grows best with plenty of moisture.

Hardiness at least from USDA zone 4 through 9.

I claim:

1. A new cultivar of hardy herbaceous perennial *Hibiscus* hybrid plant named 'Spinderella' as herein illustrated and described.

* * * * *